United States Patent
Borghi

[19]
[11] Patent Number: 6,113,628
[45] Date of Patent: *Sep. 5, 2000

[54] ENDOVASCULAR STENT WITH SUPPORT WIRE

[75] Inventor: Enzo Borghi, Budrio, Italy

[73] Assignee: AVE Galway Limited, Galway, Ireland

[*] Notice: This patent issued on a continued prosecution application filed under 37 CFR 1.53(d), and is subject to the twenty year patent term provisions of 35 U.S.C. 154(a)(2).

[21] Appl. No.: 08/952,640

[22] PCT Filed: Jun. 7, 1996

[86] PCT No.: PCT/IB96/00568

§ 371 Date: Nov. 20, 1997

§ 102(e) Date: Nov. 20, 1997

[87] PCT Pub. No.: WO96/41591

PCT Pub. Date: Dec. 27, 1996

[30] Foreign Application Priority Data

| Jun. 8, 1995 | [IT] | Italy | BO95A0292 |
| Apr. 15, 1996 | [IT] | Italy | BO96A0201 |
| Apr. 15, 1996 | [IT] | Italy | BO96A0202 |

[51] Int. Cl.$^7$ ........................................... A61F 2/06
[52] U.S. Cl. ........................ 623/1.016; 623/1.017; 606/198; 600/36
[58] Field of Search .................... 623/1, 12, 1.16, 623/1.17, 901; 606/195, 198; 600/36

[56] References Cited

U.S. PATENT DOCUMENTS

| 4,800,882 | 1/1989 | Gianturco . |
| 5,108,407 | 4/1992 | Geremia et al. ......................... 623/12 |
| 5,133,732 | 7/1992 | Witkor ..................................... 623/1 |
| 5,160,342 | 11/1992 | Reger et al. . |
| 5,383,928 | 1/1995 | Scott et al. .............................. 623/12 |
| 5,554,181 | 9/1996 | Das ........................................... 623/1 |
| 5,643,312 | 7/1997 | Fischell et al. ......................... 623/12 |
| 5,769,887 | 6/1998 | Brown et al. ............................. 623/1 |
| 5,800,515 | 9/1998 | Nadal et al. ............................. 623/1 |
| 6,015,429 | 1/2000 | Lau et al. ............................... 606/198 |

FOREIGN PATENT DOCUMENTS

| 0335341 | 10/1989 | European Pat. Off. . |
| 0540290 | 5/1993 | European Pat. Off. . |
| 0603959 | 6/1994 | European Pat. Off. . |
| 0669114 | 8/1995 | European Pat. Off. . |
| WO 9306792 | 4/1993 | WIPO . |

*Primary Examiner*—Paul B. Prebilic
*Attorney, Agent, or Firm*—Sterne, Kessler, Goldstein & Fox PLLC

[57] ABSTRACT

An endoluminal stent is formed in a modular construction to include an elongate spine and a plurality of generally tube-defining modules attached to the spine in a longitudinally sequenced array. Each module defines, in cooperation with the spine, a closed ring-like structure, with the modules being aligned in an array to define a generally tubular structure. Each of the modules is radially expandable from a reduced diameter, low profile configuration, in which it is readily navigated through the body passages, to an expanded diameter engageable with the inner luminal surface of the body lumen. The stent, being of modular construction, can be built to individual specifications for specific procedure in a specific patient. Modules are formed from a wire shaped in a flat serpentine configuration that is then wrapped in a cylindrical configuration with its free ends connected to the spine. The modules are expandable, as by a balloon, from a low profile to an expanded configuration. During expansion, the modules can wipe against the inner surface of the lumen to smooth sharp points or edges. The spine of the stent defines a substantially greater mass than that of the individual modules such that the spine can be readily observed under X-ray or fluoroscopy. The modular construction enables a wide range of variation in the characteristics of the stent, including longitudinal flexibility and radial expansion characteristics, among others.

26 Claims, 3 Drawing Sheets

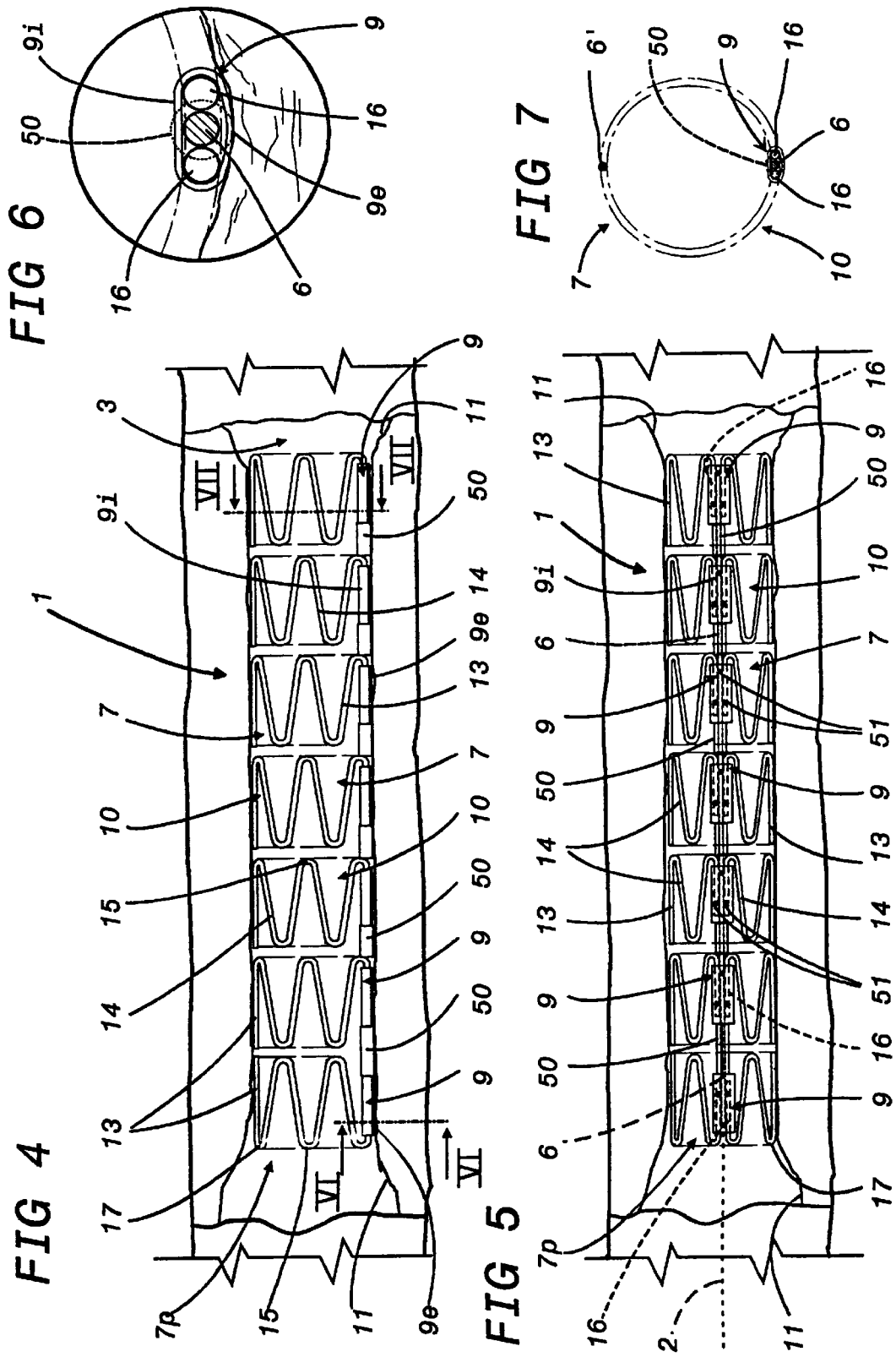

ENDOVASCULAR STENT WITH SUPPORT WIRE

BACKGROUND OF THE INVENTION

A number of medical procedures involve or can be supplemented with the placement of an endoluminal prostheses, commonly referred to as a stent, that can be implanted in a lumen, such as a blood vessel or other natural pathway of a patient's body. Such stents typically define a generally tubular configuration, and are expandable from a relatively small diameter (low profile) to an enlarged diameter. In its low profile configuration, the stent can be advanced endoluminally, by a delivery device, through the body lumen to the site where the stent is to be placed. The stent then can be expanded to a larger diameter to firmly engage the inner wall of the body lumen. The delivery device then is removed, leaving the implanted stent in place. In that manner, the stent may serve to maintain open a blood vessel or other natural duct, the functioning of which had become impaired as a result of a pathological or traumatic occurrence.

Among the medical procedures in which stents have had increasing use is in connection with percutaneous transluminal angioplasty (PTA), and particularly percutaneous transluminal coronary angioplasty (PTCA). PTA and PTCA involve the insertion and manipulation of a dilating catheter through the patient's arteries to place the dilatation balloon of the catheter within an obstructed portion (stenosis) of a blood vessel. The balloon then is expanded forcibly within the obstruction to dilate that portion of the blood vessel thereby to restore blood flow through the blood vessel. Among the more significant complications that may result from such angioplasty is that in a significant number of cases, the dilated site again becomes obstructed. By placing a stent within the blood vessel at the treated site, the tendency for such restenosis may be reduced. Accordingly, a number of stents have been proposed and developed.

One such stent is disclosed in U.S. Pat. No. 4,800,882 (Gianturco) in which a tubular stent is formed from a single, continuous metal wire that is bent into a planar serpentine configuration extending longitudinally along what will become the axis of the stent. The transversely extending loops of the serpentine wire then are deformably wrapped circumferentially about the axis to define a generally cylindrical surface and the tubular configuration. The stent so formed may be considered to define a plurality of circumferentially curved C-shaped segments, each connected to its adjacent segment at a reversing bend, so that each curved section extends in the opposite circumferential direction than its adjacent curved sections. Consequently, none of the C-shaped curved segments defines a closed circumferential loop. The endoprosthesis then is mounted about the balloon of a delivery catheter and the stent then is crimped about the deflated balloon to its low profile configuration. With the stent so mounted on the balloon, the catheter and stent are advanced through the patient's vasculature to the stenosis where the balloon is inflated to dilate and expand the stent radially and plastically to the dimensions intended. The C-shaped configuration of the curved segments of the stent necessarily and undesirably limits the resistance of the stent to radial compression, as can occur within an artery after an angioplasty has been performed. Increasing the radial resistance to contraction by increasing the thickness of the wire from which the stent is made is an unsatisfactory solution because that necessarily will require an increase in the thickness of the stent which will narrow the cross-section of the lumen. Moreover, the discontinuities in the lateral surface defined by the stent may tend to disturb the fluid dynamics of blood flowing through the blood vessel that, in turn, could induce turbulence with resulting generation of emboli, thrombi and other serious complications.

Also among the difficulties with the above-described device is that it presents little protection for the balloon of the delivery catheter when the catheter is advanced through the patient's vasculature to the deployment site. As the stent and delivery catheter are advanced, the relatively open configuration of the stent exposes the balloon to the walls of the blood vessel. Those walls may have rigid encrustations of arteriosclerotic plaque that can be irregular and sharp. Consequently, when the stent is advanced past plaque formations, the balloon may be punctured or damaged. That may result in bursting of the balloon when it is subsequently inflated, presenting a danger to the patient.

Also among the difficulties presented with the above-described stent is that its single wire construction does not readily lend itself to precise matching to the vascular anatomy or pathological situation of the specific patient in whom the stent is to be placed. The construction is adapted, as a practical matter, only to being manufactured in standard lengths. When a standard length of stent does not ideally match the patient's anatomy, the physician must choose among those standard lengths in an effort to select one or more. That is, at best, a compromise.

Still another disadvantage of the stent design described above, as well as other stent designs that have a fixed configuration (see, for example, the stent disclosed in EP 335,341) is that when the endoprosthesis must be positioned near a branch in the blood vessels, the implantation of the endoprosthesis in one of the branches may obstruct flow into the other branch.

It also is important that the location and position of the endoprosthesis be determined during implantation as well as at a later time. The Gianturco stent described above, being formed from a single, slender wire may be difficult, if not impossible, to visualize under fluoroscopy or X-ray.

It is among the general objects of the invention to provide an improved endovascular stent that overcomes the above disadvantages.

SUMMARY OF THE INVENTION

In accordance with the invention, a stent is constructed in a modular fashion to include an elongate spine and a plurality of generally tube-defining modules attached to the spine in a longitudinally sequenced array. Each module defines, in cooperation with the spine, a closed ring-like structure, with the modules being aligned in an array to define a generally cage-like tubular structure. Each of the modules is formed from wire and is radially expandable from a reduced diameter, low profile configuration, to an expanded diameter engageable with the inner luminal surface of the blood vessel or other body lumen. The modules may be individually mounted and secured in succession along a support wire and are positioned at selected intervals along the support wire.

In another aspect of the invention, each individual tubular module is formed from a wire shaped in a serpentine configuration defined by a plurality of elongate wire segments connected end-to-end by shorter segments. The serpentine wire is wrapped in the generally cylindrical configuration of the module and its free ends are connected to the spine. The elongate segments of each module are essentially oriented lengthwise along the spine and, in transverse section, define the locus of a closed curved loop. When the module is in its low profile configuration, its elongate segments lie closely adjacent and generally parallel to each other and to the spine.

In another aspect of the invention, the modules can be disposed along the spine so that when in a low profile configuration their adjacent ends can be disposed in close proximity to each other to define a circumferential envelope that extends substantially continuously in a longitudinal direction to contain and protect the balloon received within the tubular array of modules. When the anatomy into which the device is to be placed permits the use of a continuous series of such modules, the balloon can be protected over its full length.

In still another aspect of the invention, the modules can be assembled along the spine at selected locations and spacing, enabling a stent to be easily constructed to fit the specific vessel anatomy of the patient.

In a further aspect of the invention, the expansion of the modules from a low profile to an expanded configuration causes the longitudinal segments of the modules to wipe against the inner surface of the lumen wall to smooth sharp points or edges of the blood vessel thereby to reduce the risk of balloon rupture.

In an additional aspect of the invention, the spine is formed to have a substantially greater mass than that of the individual modules such that the spine can be readily observed under X-ray or fluoroscopy.

In still another aspect of the invention, the spine, to which the modules are attached, may be considered as including the support wire and a plurality of connectors individually mountable on the support wire and in which the connectors also serve to attach the ends of the wire of the module to each other and to the support wire. The connectors are configured to provide a region of increased mass by which the spine can be viewed radiographically.

In an additional aspect of the invention, tubular spacers may be disposed on the support wire between the connectors to define the desired spacing between the modules as well as to provide a continuously radiographically observable spine.

It is among the general objects of the invention to provide an improved endoprosthesis embodying a modular construction.

A further object of the invention is to provide a modular endoprosthesis that can be easily constructed to a selected configuration adapted for use in a specific patient vascular anatomy.

Another object of the invention is to provide a stent that is readily observable radiographically.

An additional object of the invention is to provide a construction for a stent in which obstruction of side branches can be minimized.

A further object of the invention is to provide a balloon expandable stent in which the stent provides protection for the balloon as the balloon is navigated into position in the blood vessel.

DESCRIPTION OF THE DRAWINGS

The foregoing and other objects and advantages of the invention will be appreciated more fully from the following description thereof, with reference to the accompanying drawings wherein:

FIG. 4 is a partially diagrammatic side illustration of the stent disposed within a blood vessel and incorporating several modifications;

FIG. 5 is an illustration similar to FIG. 4 in which the spine is illustrated in plan;

FIG. 6 is a sectional illustration of the region of the spine as seen along the line VI—VI of FIG. 4;

FIG. 7 is a diagrammatic sectional illustration of the device as seen along the line VII—VII of FIG. 4;

DESCRIPTION OF THE ILLUSTRATIVE EMBODIMENTS

Figure 1:
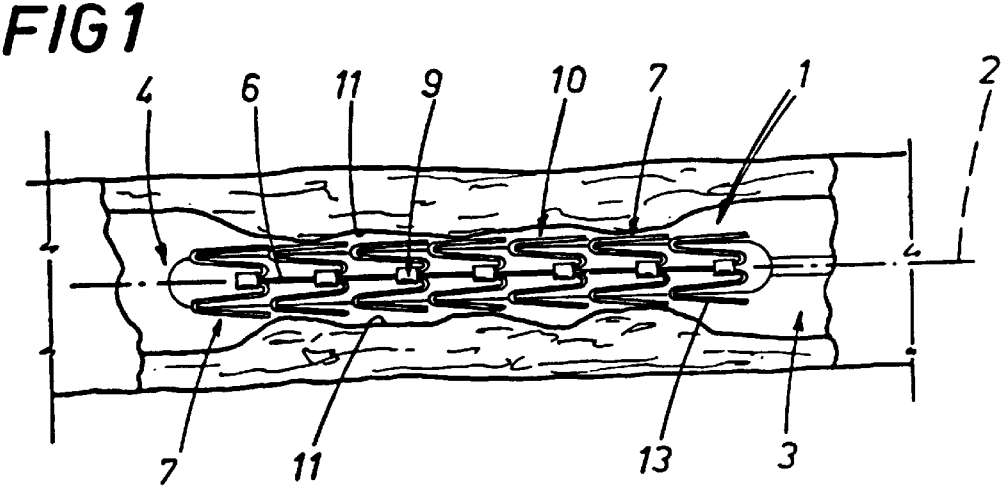
FIG. 1 is a somewhat diagrammatic illustration of an endoprosthesis in accordance with the invention disposed within an obstructed portion of a blood vessel with the endoprosthesis in its low profile, unexpanded configuration.
Figure 2:
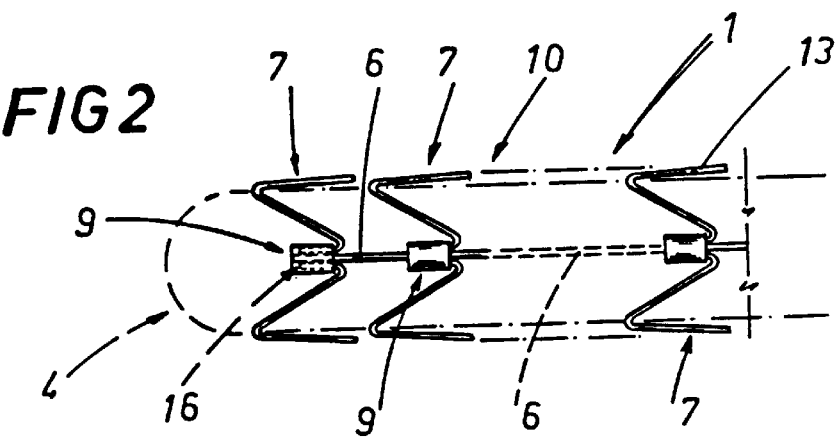
FIG. 2 is a somewhat diagrammatic illustration of the endoprosthesis disposed on a balloon that has been inflated to expand the prosthesis to a larger diameter.
Figure 3:
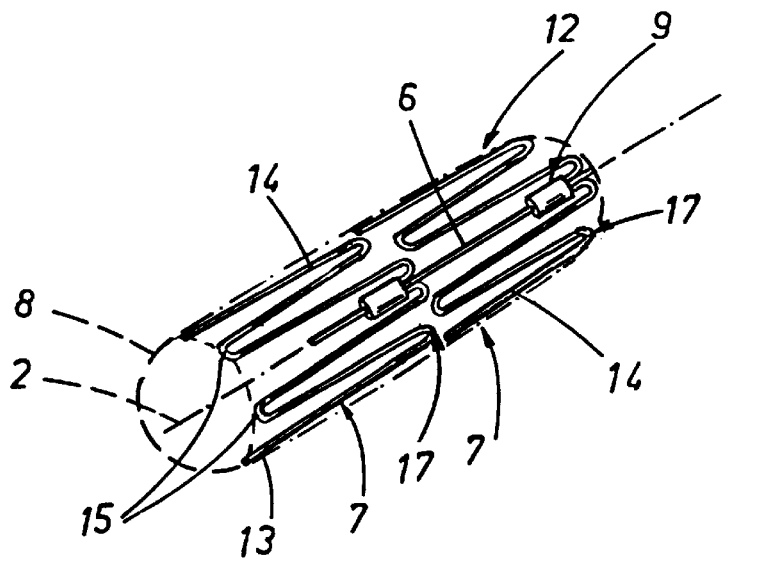
FIG. 3 is a somewhat diagrammatic illustration of a pair of adjacent modules of the endoprosthesis illustrating their connection to the support wire.

FIG. 1 illustrates the endoprosthesis 1 that may be considered to define a cage-like tubular arrangement formed from wire-like components and having a central longitudinal axis 2. The endoprosthesis 1 is constructed from a plurality of individual modules 7 connected to each other along a spine that may be considered to include a longitudinal support wire 6 and connectors 9. The modules 7 are expandable from a contracted, low profile configuration, to facilitate placement of the stent in the body lumen, to an enlarged diameter as suggested in FIG. 2, by which the modules can be expanded into firm engagement with the inner surface of walls 11 of the body lumen 3 to maintain the body lumen open to facilitate blood flow. In the preferred embodiment, the module is expandable inelastically. The radially expandable generally tubular modules 7 are mounted and aligned in a longitudinally sequenced array on the support wire 6 by a connector 9 associated with each of the modules 7. The modules, when mounted on the support wire 6 may be considered to define a virtual peripheral surface 12 that, in transverse cross-section, is in the form of a virtual closed curve or loop 8 about the longitudinal axis 2.

Each module 7 is formed from a wire 13 shaped and configured to enable radial expansion of the cylindrical peripheral surface 12. The module may be formed by first forming the wire 13 into a flat serpentine configuration and then wrapping the serpentine wire into its looped configuration. The terminal ends 16 of the serpentine wire are free. The free ends 16 of the wire 13 may be attached to each other and to the support wire 6 by the connector 9. The serpentine arrangement of each of the modules may be considered to include a series of elongate first segments alternated with and connected by bends that may be curved (e.g., circular) or may comprise shorter connective segments 15 connected to the elongate segments 14 at cusps 17. The connective bends between the longitudinal segments 14 may lie along and define a locus of the closed loop 8. Preferably, the wire 13 is formed so that the arrangement of bends will be uniformly circumferentially spaced about the virtual closed loop 8 to provide the modules 7 with uniform strength in directions transverse to the support wire 6.

Figure 8A:
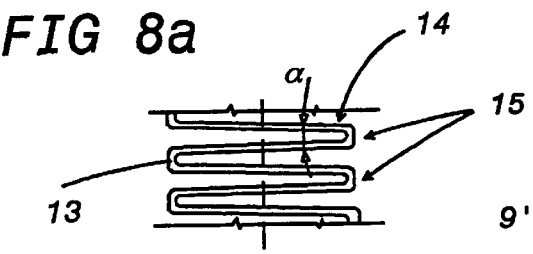
FIGS. 8A–8C illustrate schematically the manner in which the configuration of the modules change as they are expanded from the low profile configuration to an expanded configuration.
Figure 8B:
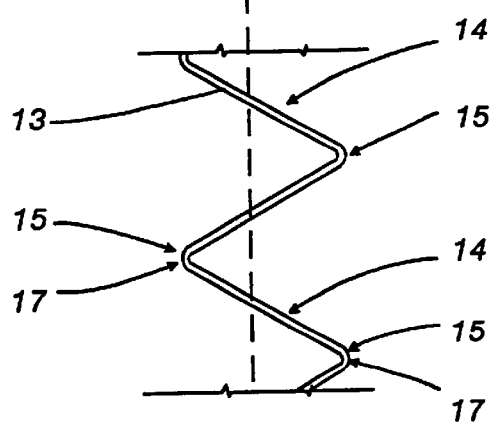
Figure 8C:
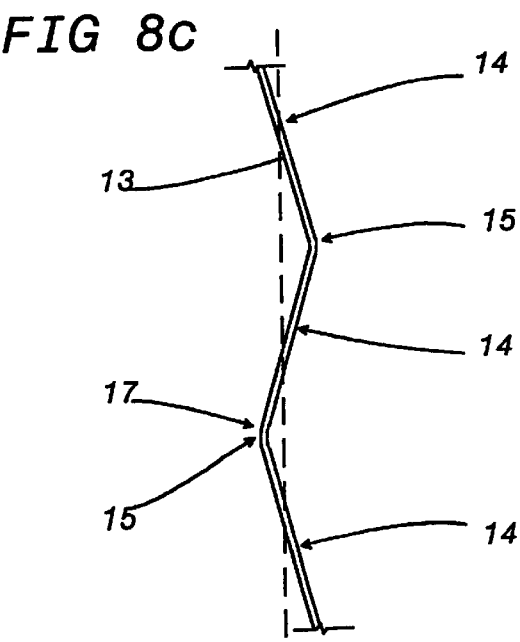

As illustrated diagrammatically in FIG. 8, when the modules are in their low profile, unexpanded configuration, the bends 15, 17 that define the connection between adjacent elongate segments 14 are such that the elongate segments 14 will lie at an angle α close to zero and at an angle approaching 180° when the module is expanded to a position of maximum expansion as suggested in FIG. 8(c). It should be understood, however, that in practice, the stent preferably should not be expanded beyond a configuration suggested in FIG. 8(b). Preferably, the angle α defined between adjacent elongate segments 14 should be contained between about 45° to about 85°. The configuration of the connective bends, including the cusps 17 may be varied to vary the angle α or to vary their number circumferentially about the closed curve 8 to vary the characteristics of the modules 7 including varying its resistance to compressive radial loads such that the endoprosthesis can further be tailored and made to conform ideally to the specific body lumen 3 in which it is to be implanted.

By way of illustrative example only, a stent may be provided to include modules 7 formed from wire having a diameter of about 0.15 millimeter with elongate segments 14 (not including the connective bends between adjacent segments 14) of a length of about 1.8 millimeters. When the connective bends between adjacent elongate segments 14 are smoothly curved, they may have a radius of about 0.15 millimeter before expansion. A stent having the foregoing dimensions can be expected to be expandable to diameters between about 2.5 to about 4.0 millimeters without excessive expansion, and that such stent exhibits substantial resistance to radial collapse that is well above the maximum radial compressive loads that can be expected to be imposed on the stent by contraction of an artery having a luminal diameter of about 2.5 to about 4.0 millimeters.

In the preferred embodiment the connectors 9 may be constructed to be mounted on the longitudinal support wire 6, as by threading them on the wire 6. The connector 9 preferably may comprise a ring that defines sufficient internal space to receive and circumscribe the free ends 16 of the wire 13 while also permitting firm connection of the ring to the longitudinal support wire 6. The ring connector 9, free ends 16 of the wire and support wire 6 may be firmly connected by means of a permanent deformation, such as crimping, or may be attached to each other by spot welding. As suggested at points 51 in FIG. 5, laser spot welding is preferred. When assembled using laser spot welding, it is preferred that the terminal portions 16 of the module 7 are first welded to the ring 9 and the ring 9 then is welded to the support wire 6. In some instances, it may be desirable to modify the stent so that one or more of the modules (but not the endmost modules) are not securely attached to the support wire 6 but, instead, are permitted some freedom of sliding movement along the support wire 6. This enables making of a final adjustment to the position of the module after the device has been placed in the patient's blood vessel, should that be desired.

Figure 6A:
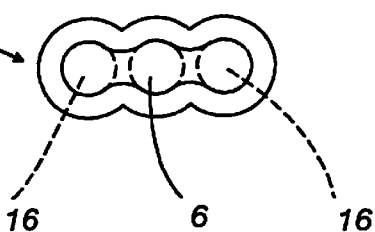
FIGS. 6A illustrates in transverse cross-section, another embodiment of the connector ring for connecting a module to a support wire.

FIG. 6 illustrates, in further detail, the configuration of one embodiment of the ring 9. As shown, the ring 9 may be considered to have an internal face 9i that may be essentially flat and an outside face 9e that may be rounded to adapt more readily to the generally cylindrical wall of the blood vessel. It should be understood, however, that the inner and outer faces 9i, 9e could be fashioned either to be flat or rounded. FIG. 6A illustrates the cross-section of another embodiment of the connector ring 9' in which the wall of the ring is formed to define an inner arcuate contour corresponding to the contours of the support wire 6 and free ends 16 of the module 7. The outer surface of the ring in this embodiment may have a paralleling contour.

The foregoing construction enables a stent to be specially assembled to conform accurately to the specific anatomy of the patient in whom the stent is to be placed. The modules can be positioned as desired along the support wire 6 and can be secured in that configuration. The support wire 6 may be selected to provide the desired degree of longitudinal flexibility and may be made from wire that is extremely flexible to facilitate positioning of the device in relatively inaccessible body lumen. With the foregoing construction in which the stent has an independent support wire 6, the degree of stiffness or flexibility of the support wire can be selected independently of the wire from which the tubular modules are formed. The support wire 6 may be highly flexible to enable the stent to be carried through narrow, tortuous vessels, such as coronary arteries.

It should be understood that although the presently preferred embodiment of the invention incorporates a metal support wire 6 (e.g., stainless steel), the modular construction of the invention enables a fabrication of a stent in which the support wire may be formed from non-metallic materials, such as polymeric materials, for example, nylon. Other mechanically and biologically suitable classes of materials may be selected, including materials from among those that are biologically absorbable into the tissue of the vessel wall over time. With a bioabsorbable support wire 6, it should be selected to maintain its desirable mechanical characteristics for a sufficient time to enable the modules 7 to become firmly embedded in the vessel wall. Thus, the modular construction of the invention provides a substantially increased range of materials and properties for the individual components, each being selected to provide optimum results.

The connecting rings 9, especially when assembled about the two end segments 16 of the modules 7 and the support wire 6, present a significantly greater mass than that of the wire 13 from which the modules are fashioned. Thus, the region of the spine that includes the connecting rings 9 will present substantially greater radiopacity than that presented by the wire 13 of the associated module. The substantially increased radiopacity of the connected region enhances substantially the radiographic control of the endoprosthesis 1 during implantation. It also enables the endoprosthesis to be observed radiographically at a later time without requiring use of ultrasound procedures. The configuration of the stent enables the tubular frame 10 to be constructed to have a high mechanical strength while enabling expansion of the device between its low profile and expanded configuration yet in which the wire 13 of the modules 7 will be substantially transparent to X-rays at radiation levels that are typically used in such procedures.

FIGS. 4–6 illustrate a further feature of the invention in which the stent 1 can be provided with spacers 50 disposed between pairs of successive rings 9 before the rings are secured to the support wire 6. The spacers preferably are cylindrical in shape and have a central hole by which the spacers can be slid, in bead-like fashion, onto and along the longitudinal wire 6. When a series of connectors 9 and spacers 50 have been placed on the support wire 6, each successive pair of connectors 9 or spacers 50 may embrace one of the other. The length of the spacer(s) may be predetermined to enable precise control over the spacing between two successive modules as well as to reduce the risk of the support wire 6 being twisted or otherwise becoming damaged. An additional result that can be achieved by using the spacers 50 is that it enables a stent to be assembled with only the two endmost connectors 9 anchored securely to the support wire 6. In such an embodiment, the intermediate components (the connectors 9 and spacers 50) will be retained in position on the support wire and will not separate.

Whether all or only the endmost connectors 9 are secured to the longitudinal support wire 6, the intermediate spacers 50 need not be directly secured to the wire 6 but, instead, can be retained in place by and between their adjacent connectors 9. By way of dimensional example, the cylindrical spacers that may be used with a device having the above described dimensions may be about 1.10 millimeters in length, 0.30 millimeter in outer diameter and having a wall thickness of about 0.075 millimeter.

The spacers 50, being circular in cross-section may be arranged to lie substantially flush with the rounded outside face 9e of the adjacent connecting ring 9 as shown in FIG. 6. The spacers 50 may remain marginally proud of the inside face 9i of the connectors 9 as shown in FIGS. 4 and 6. When used with a connector 9 as illustrated in FIG. 6A, the outer surface of the spacer may define a continuation of the outer curved contour in the middle section of the connector 9.

A further advantage in the use of spacers 50 is that together with the rings and the portions of the wire that extend through the rings, the arrangement defines a spine that presents a substantially continuous elongate mass having a radiopacity considerably greater than that of the serpentine wires 13.

All components of the device should be formed from materials that are compatible with each other and will not form microcells that might give rise to electrochemical corrosion of any part of the device after it has been implanted into the blood vessel. The longitudinal support wire 6, wire 13 and connector 9 should have the same chemical composition. Exemplary materials that are preferable in making the endoprosthesis include those from the group of annealed stainless steels, titanium alloys, gold-nickel alloys, nickel-chromium alloys, and titanium-chromium alloys.

The support wire 6 and modules 7 may be treated and formed to vary the mechanical and functional characteristics independently of each other to obtain a desired configuration adapted to treat the anatomy of a specific patient. For example, the wire 13 from which the module is formed may be subjected to an annealing heat treatment to control the malleability of the wire.

Also among the characteristics of the invention is the manner in which the tubular modules 7 protect the balloon of a balloon catheter 4 used in the placement of the endoprosthesis 1. When the device is mounted on the folded balloon of the catheter and is in its low profile phase adapted for delivery, the elongate segments 14 will be disposed in close, substantially parallel and close proximity to each other circumferentially about the balloon. Additionally, the individual tubular modules can be arranged in close longitudinal proximity so that the balloon can be fully protected within the stent longitudinally as well as circumferentially. After the device and catheter 4 have been navigated to locate the deployment site, expansion of the device causes the elongate segments 14 to spread and expand circumferentially along the walls 11 to the body lumen 3 to wipe against the walls 13 and smooth surface roughness that may be present including, particularly, smoothing of sharp or hard regions that otherwise could damage the balloon and possibly result in balloon puncture. As the segments 14 of the module wipe against the walls 11 of the passage 3, they effect a significant shearing action.

In the example illustrated in FIGS. 4 and 5, the endmost tubular modules are arranged in a reversed configuration. As shown, the first tubular module 7p on the left of that example is reversed such that the terminal portions 16 of the wire 13 are directed toward the opposite end of the device, that is, toward the adjacent spacer 50. The reversed arrangement lessens the risk that sharp edges may main exposed or that a crevice within the endmost connector may be presented to the blood flow. Such a crevice could become invested with blood from facing the blood flow and could result in the development of a localized thrombosis that could lead to restenosis of the lumen.

FIG. 7 illustrates diagrammatically a further modification in which a second support wire 6' is positioned diametrally opposite the first support wire 6. The addition of a second support wire may make the stent more secure as well as to provide a second highly radiopaque spine to further facilitate localization of the stent during examination. The second support wire 6' is connected to each module in the same manner as with the first support wire 6. In order to accommodate the second support wire 6', the module 7 is formed from two serpentine wires each arranged about the longitudinal axis 2 of the stent to define a portion of the virtual cylindrical surface 12. Each partially curved module segment includes two free ends 16, each adapted to be received within its respective connector 9.

If desired, the wires embodied in the stent may be coated with a protective material such as carbon or with an anti-coagulant substance such as heparin.

Figure 9:
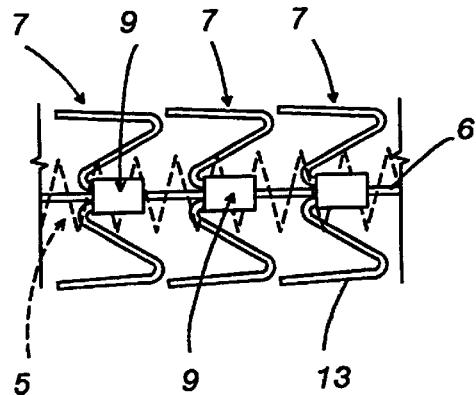
FIG. 9 illustrates, diagrammatically, a portion of a stent expandable by alternative means.

In a further alternative embodiment, the stent may be expandable by other means, for example, by forming the module 7 from a shape memory alloy such as nitinol. The stent may be provided with electrical resistance heaters 5 to generate sufficient heat to induce thermally controlled expansion of the shape memory alloy module. Such a device is illustrated schematically in FIG. 9.

It should be understood that the foregoing description of the invention is intended merely to be illustrative thereof and that other embodiments, modifications and equivalents thereof will be apparent to those skilled in the art without departing from its principles.

What is claimed is:

1. An endoprosthesis for a body lumen comprising:
   an elongate support wire; and
   a plurality of modules supported on the support wire at sequential locations along the support wire, each of the plurality of modules being connected to the support wire by a connector secured to the module and attached to the support wire,
   wherein each module of the plurality of modules defines a closed circumferential loop, the modules being arranged on the support wire to define a generally tubular configuration, and
   wherein the modules are constructed to be expandable from a radially contracted configuration in which the endoprosthesis can be positioned in the body lumen to a radially expanded configuration, and
   wherein each module is formed from a serpentine wire having a plurality of elongate segments alternated with shorter connective bends, and
   wherein the serpentine wire has free terminal ends attached to the connector to secure the module in its closed circumferential loop configuration, and wherein the connector includes an aperture receptive to the support wire and the free terminal ends of the serpentine wire of the associated module.

2. An endoprosthesis as defined in claim 1 wherein the connector comprises a ring adapted to surround each of the free terminal ends of its associated module and the support wire.

3. An endoprosthesis as defined in claim 2 wherein the module, connector and support wire are connected by one of or a combination of spot welding and crimping.

4. An endoprosthesis as defined in claim 1 wherein a radially outward facing surface of the connector is curved to facilitate its conformance to the curved shape of a wall of the body lumen.

5. An endoprosthesis for a body lumen comprising:

an elongate support wire;

a plurality of modules supported on the support wire at sequential locations along the support wire, each of the modules being connected to the support wire by a connector secured to the module and attached to the support wire;

each module defining a closed circumferential loop the modules being arranged on the support wire to define a generally tubular configuration;

the modules being constructed to be expandable from a radially contracted configuration in which it can be positioned in the body lumen to a radially expanded configuration;

a spacer mounted on the support wire between at least one pair of modules;

wherein an outer surface of the spacer is curved to facilitate its conformance to the curved shape of a wall of the body lumen.

6. An endoprosthesis as defined in claim 5 wherein the outwardly exposed surface of the spacer is contoured to correspond substantially to the contour presented by the outwardly facing surface of its adjacent connectors thereby to present a substantially smooth and continuous surface adapted to bear against and conform with the contour of the body lumen.

7. An endoprosthesis as defined in claim 1 wherein the end modules of the endoprosthesis are attached to the support wire with their free terminal ends oriented toward each other.

8. An endoprosthesis as defined in claim 2 wherein the internal contour of the ring is adapted to surround closely and substantially conform to the external contour of the free terminal ends and support wire.

9. An endoprosthesis as defined in claim 1, wherein an angle is formed between adjacent elongate segments of said plurality of elongate segments of said at least one module.

10. An endoprosthesis as defined in claim 9, wherein said angle is between 45 degrees and 85 degrees when said at least one module is in said radially expanded configuration.

11. An endoprosthesis as defined in claim 1, further comprising a spacer mounted on said support wire between at least one pair of modules.

12. An endoprosthesis as defined in claim 11, wherein said spacer has a greater mass than said modules.

13. An endoprosthesis as defined in claim 1, wherein a region of connection between each of said modules and said support wire has a mass with greater radiopacity than said expandable modules.

14. An endoprosthesis as defined in claim 11, wherein an outer surface of said spacer is curved to facilitate its conformance to the curved shape of a wall of the body lumen.

15. An endoprosthesis as defined in claim 1, wherein said bends are arranged in a substantially uniform circumferential distribution along the locus of the closed loop.

16. An endoprosthesis as defined in claim 1, further comprising a second longitudinal wire connected to said modules and extending general parallel to said support wire.

17. An endoprosthesis as defined in claim 1, wherein said modules and said support wire have different malleability.

18. An endoprosthesis as defined in claim 1, wherein said module is formed from a material belonging to the group comprising annealed steel, titanium alloys, nickel gold alloys, nickel chromium alloys, and titanium chromium alloys.

19. An endoprosthesis as defined in claim 1, wherein the endoprosthesis is coated with a protective material.

20. An endoprosthesis as defined in claim 19, wherein said protective material comprises carbon.

21. An endoprosthesis as defined in claim 1, wherein the endoprosthesis is coated with a drug.

22. An endoprosthesis as defined in claim 21, wherein said drug comprises an anticoagulent.

23. An endoprosthesis as defined in claim 1, wherein the endoprosthesis is dimensioned to be receivable in a human coronary artery when in said radially contracted configuration and engages inner walls of said artery when in said radially expanded configuration.

24. An endoprosthesis as defined in claim 1, wherein said connector further comprises a ring having an inside face and an opposite outside face, said outside face being rounded and adapted to conform to a nominally cylindrical wall of the body lumen.

25. An endoprosthesis as defined in claim 24, wherein said inside face of said ring is substantially flat.

26. An endoprosthesis as defined in claim 24, further comprising a spacer disposed on said support wire adjacent said connector, an external surface of said spacer defining a rounded profile substantially corresponding to said rounded outside face of said connector.

* * * * *